(12) United States Patent
Pan

(10) Patent No.: US 12,053,570 B2
(45) Date of Patent: Aug. 6, 2024

(54) NASAL ASPIRATOR SUCTION BIN ASSEMBLY

(71) Applicant: Ling Pan, Mianyang (CN)

(72) Inventor: Ling Pan, Mianyang (CN)

( * ) Notice: Subject to any disclaimer, the term of this patent is extended or adjusted under 35 U.S.C. 154(b) by 0 days.

(21) Appl. No.: 17/827,831

(22) Filed: May 30, 2022

(65) Prior Publication Data

US 2022/0288295 A1    Sep. 15, 2022

(51) Int. Cl.
*A61M 1/00*    (2006.01)

(52) U.S. Cl.
CPC ................ *A61M 1/65* (2021.05); *A61M 1/87* (2021.05); *A61M 2210/0618* (2013.01)

(58) Field of Classification Search
CPC ........... A61M 1/65; A61M 1/87; A61M 1/78; A61M 1/60; A61M 1/682; A61M 1/68; A61M 1/684; A61M 2210/0618; A61B 5/6819; A61B 1/233; A61B 2017/246; A61B 17/1688; A61B 2018/00327
See application file for complete search history.

(56) References Cited

U.S. PATENT DOCUMENTS

| | | | | | |
|---|---|---|---|---|---|
| 4,995,386 | A | * | 2/1991 | Ng | A61M 1/60 604/319 |
| 5,649,530 | A | * | 7/1997 | Ballini | A61M 11/06 604/35 |
| 7,959,597 | B2 | * | 6/2011 | Baker | A61M 1/772 604/28 |
| 2002/0198488 | A1 | * | 12/2002 | Yao | A61M 1/78 604/35 |
| 2009/0076441 | A1 | * | 3/2009 | Sebban | A61M 3/022 604/35 |
| 2015/0283322 | A1 | * | 10/2015 | Hachey | A61M 5/002 604/506 |
| 2022/0143294 | A1 | * | 5/2022 | Wei | A61M 1/64 |
| 2022/0296800 | A1 | * | 9/2022 | Ou Yang | A61M 1/87 |
| 2022/0395625 | A1 | * | 12/2022 | Ye | A61M 1/64 |

* cited by examiner

*Primary Examiner* — Benjamin J Klein
*Assistant Examiner* — Hans Kaliher
(74) *Attorney, Agent, or Firm* — Jose Cherson Weissbrot

(57) ABSTRACT

A nasal aspirator suction bin assembly comprises a suction bin base, which has a first connecting end connected with a host and a second connecting end connected with a suction bin cover; after the suction bin base is connected with the suction bin cover, a cavity is formed therein; the middle of the suction bin base is provided with an outlet tube, which runs through the suction bin base and extends into the cavity; the upper end of the suction bin cover is provided with a suction tube, which runs through the suction bin cover and extends into the cavity; a bracket is arranged in the cavity, and the bracket comprises a bracket tube which can be inserted on the outlet tube and a baffle arranged at the other free end of the bracket tube, and at least one air hole is arranged on the bracket tube to keep the suction tube and the outlet tube in communication all the time; the cavity is used to store the inhaled nasal fluid. Because of the umbrella-shaped bracket, the nasal fluid cannot touch the position of the air hole during normal use and small-angle inclined use, so the nasal fluid cannot enter the host and cause pollution.

8 Claims, 6 Drawing Sheets

NASAL ASPIRATOR SUCTION BIN ASSEMBLY

TECHNICAL FIELD

The present application relates to a nasal aspirator suction bin assembly.

BACKGROUND

As an auxiliary tool, a nasal aspirator can aspirate nasal fluid from the nasal cavity, an d is generally used by children and the elderly who lack self-care ability. The most commonly used nasal aspirator is of a pump type, which can be further divided into electric and manual types. At present, the electric nasal aspirator is favored by more and more consumers. Generally, the electric nasal aspirator is equipped with an outlet tube connected with a host, which generates a negative pressure when the host works and vacuumizes the inside of the suction bin assembly through the outlet tube. During the use of the electric nasal aspirator, some nasal fluid will enter the host through the outlet tube, resulting in the pollution of the air returning tube and inconvenient cleaning.

SUMMARY

In view of the shortcomings in the above problems, the present application provides a nasal aspirator suction bin assembly.

In order to achieve the above purpose, the present application provides a nasal aspirator suction bin assembly, which a suction bin base, wherein the suction bin base is provided with a first connecting end connected with a host and a second connecting end connected with a suction bin cover, and the suction bin base is connected with the suction bin cover to form a cavity therein, and a middle part of the suction bin base is provided with an outlet tube, which runs through the suction bin base and extends into the cavity, and an upper end of the suction bin cover is provided with a suction tube which runs through the suction bin cover and extends into the cavity, characterized in that a bracket is arranged in the cavity, and the bracket comprises a bracket tube which can be inserted into the outlet tube and a baffle arranged at the other free end of the bracket tube; at least one air hole is arranged on the bracket tube to keep the suction tube and the outlet tube in communication all the time: the bracket further comprises a baffle I integrally formed: a cross section of the baffle I is smaller than that of the baffle: and the air hole is arranged between the baffle and the baffle I.

The cavity is used to store the inhaled nasal fluid. Because of the umbrella-shaped bracket, the nasal fluid cannot touch the position of the air hole during normal use and small-angle inclined use, so the nasal fluid cannot enter the host and cause pollution.

As a further improvement of the solution, the suction bin base and the suction bin cover are fixed by rotating and fastening, and a first sealing ring is arranged at the connecting part thereof.

In the technical solution, the first sealing ring plays a role in sealing the connecting part, and the rotary fastening mode is convenient to disassemble and assemble, and is convenient for assembly or cleaning.

As a further improvement of the solution, an outer end of the outlet tube is connected with a micro-vacuum pump of the host, an inner end of the outlet tube is flush with an enclosure plate of the suction bin base (6), and a conical surface is formed on the inner end.

In the above technical solution, a micro-vacuum pump compresses and stretches the air in the pump cavity with a fixed volume to form vacuum, forming a pressure difference, sucking nasal fluid into the cavity from the suction tube, and discharging gas from the outlet tube, and the conical surface is convenient for the assembly of the outlet tube and the bracket.

As a further improvement of the solution, the outlet tube and the suction bin base are integrally formed of a PC material, the bracket is made of the PC material, and the outlet tube is provided with a second sealing ring below the conical surface.

In the technical solution, the second sealing ring further improves the sealing performance.

As a further improvement of the solution, an upper surface of the baffle is a curved surface with a middle position and a low edge position.

In the technical solution, the curved surface design plays the role of drainage when the nasal aspirator is erected for use.

As a further improvement of the solution, the suction tube and the suction bin cover are integrally formed by the PC material, and a distance from a lower surface of the suction tube to a bottom plate of the suction bin base is the same as a height of the bracket; a lower part of the suction tube is provided with a notch.

In the technical solution, by matching the distance with the height, the bracket is prevented from shifting in the use process, which affects the use effect, and the notch is arranged to ensure the smooth airflow inside the suction tube and the cavity.

As a further improvement of the solution, the suction bin cover is made of a transparent or semitransparent material.

In the technical solution, it is made of transparent or semitransparent materials, so that users can observe the storage amount of nasal fluid in the cavity from the outside, and it is convenient for timely cleaning.

As a further improvement of the solution, an upper part of the suction tube is sleeved with a suction nozzle, the suction nozzle is made of a silica gel material, and the suction nozzle is arranged in a shape with a small top and a large bottom.

In the above technical solution, the configuration of the suction nozzle is beautiful, and the mucosa in the nasal cavity can be better protected by the function of the suction nozzle, and the suction nozzle is arranged in a shape of small top and large bottom, so as to be convenient to extend into the nasal cavity for operation.

Compared with the prior art, the present application has the beneficial effects that: the cavity is used for storing inhaled nasal drops, and due to the effect of the umbrella-shaped bracket, the nasal drops cannot touch the position of the air hole during normal use and small-angle inclined use, so the nasal drops cannot enter the host to cause pollution; The nasal aspirator has the advantages of convenient disassembly and assembly, easy cleaning, strong sealing performance and high connection strength, and the suction nozzle can well protect nasal mucosa with good comfort.

1. Suction nozzle; 2. Suction tube; 21. Notch; 3. Suction cover; 4. Bracket; 41. Bracket tube; 42. Baffle I; 4. Air hole; 44. Baffle; 5. First sealing ring; 6. Suction bin base; 61. Bottom plate; 62. Enclosure plate; 7. Second sealing ring; 8. Outlet tube.

DESCRIPTION OF EMBODIMENTS

Figure 1:
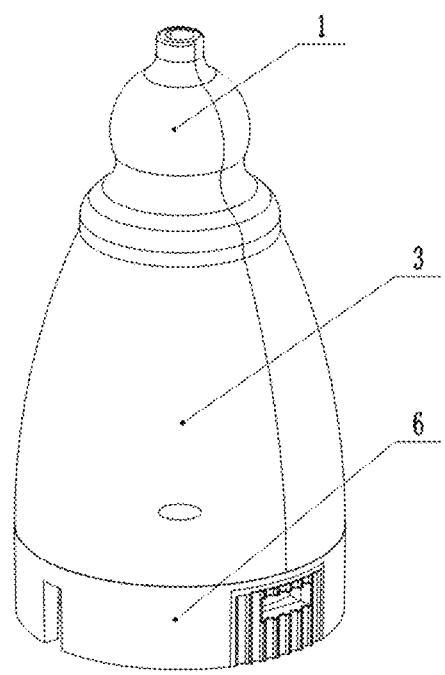
FIG. 1 is a perspective view of a nasal aspirator suction bin assembly according to the present application.
Figure 2:
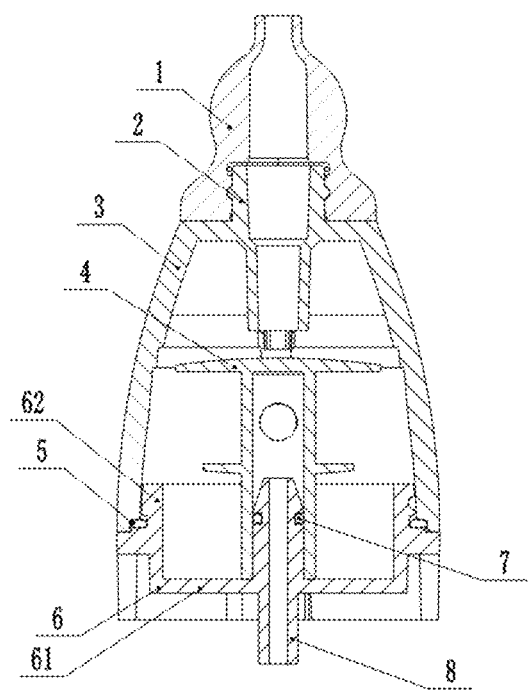
FIG. 2 is a sectional view of a nasal aspirator suction bin assembly according to the present application.
Figure 3:
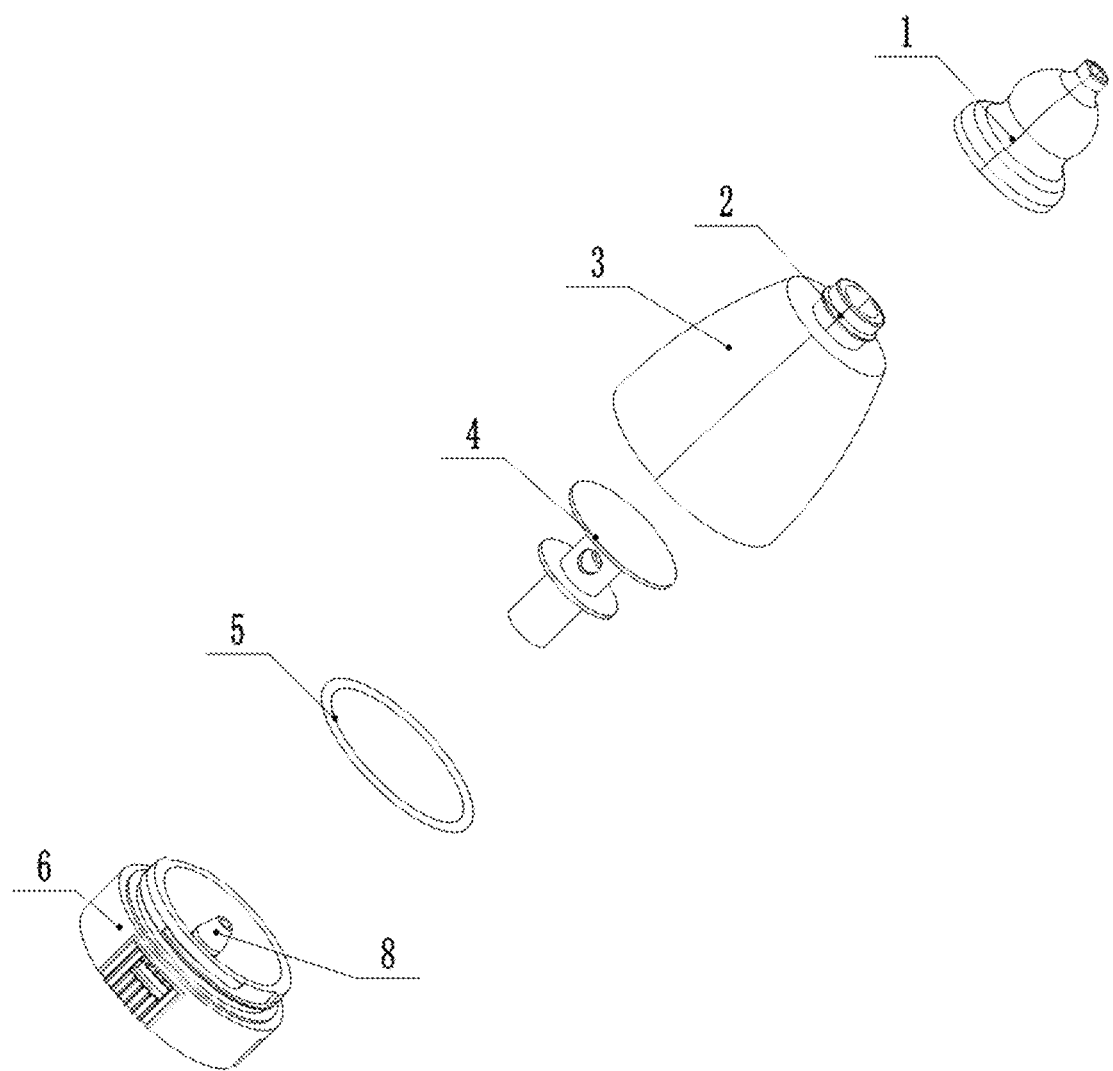
FIG. 3 is an exploded view of a nasal aspirator suction bin assembly according to the present application.
Figure 4:
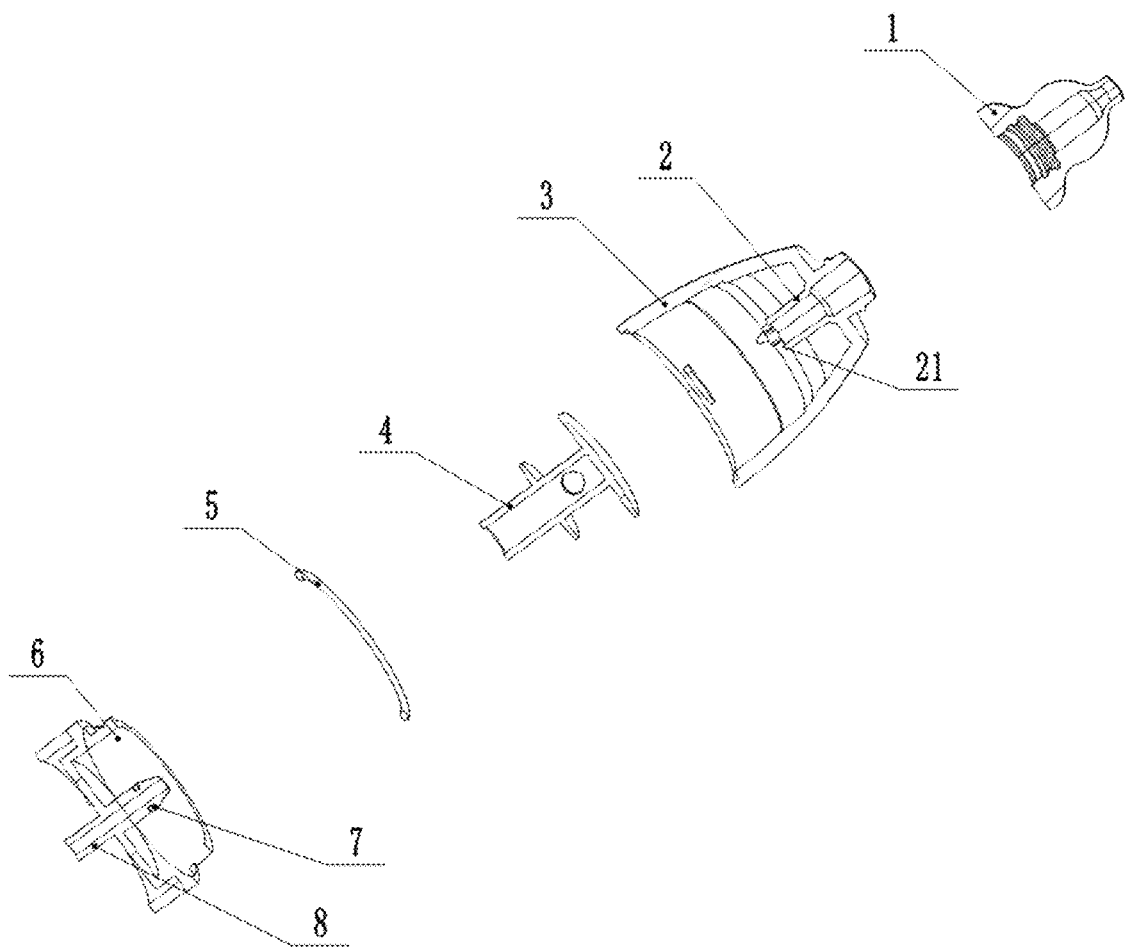
FIG. 4 is a half sectional view of FIG. 3.
Figure 5:
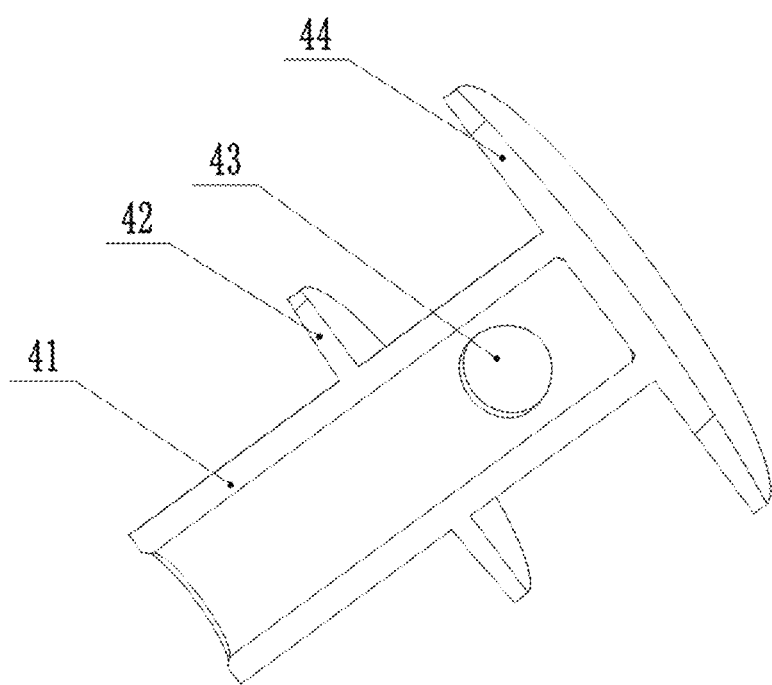
FIG. 5 is an enlarged view of the bracket in FIG. 4.
Figure 6:
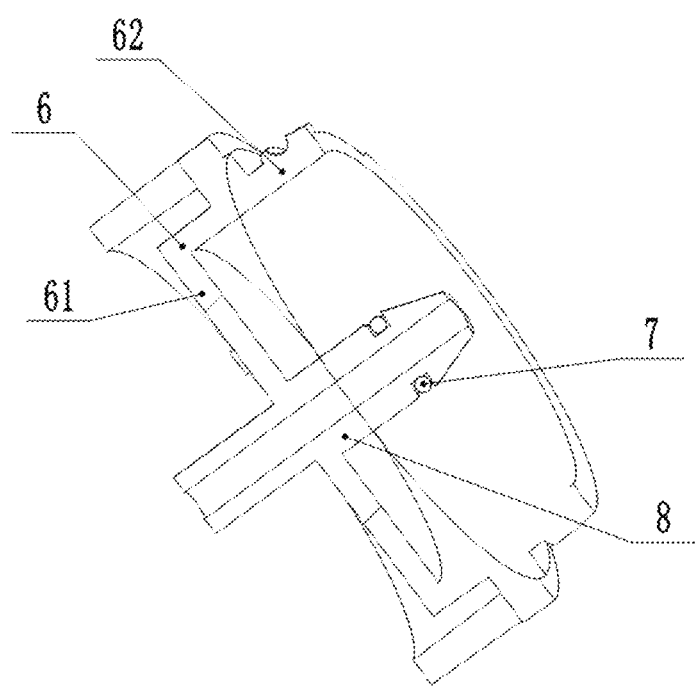
FIG. 6 is an enlarged view of the suction bin base in FIG. 4.

As shown in FIGS. 1-6, a nasal aspirator suction bin assembly according to the embodiment of the present application includes a suction bin base 6, which has a first connecting end connected to a host and a second connecting end connected to a suction bin cover 3; after the suction bin base 6 is connected with the suction bin cover 3, a cavity is formed in both of them; the middle of the suction bin base 6 is provided with an outlet tube 8, which runs through the suction bin base 6 and extends into the cavity; the upper end of the suction bin cover 3 is provided with a suction tube 2; the suction tube 2 penetrates through the suction bin cover 3 and extends into the cavity, and the cavity is internally provided with a bracket 4, which includes a bracket tube 41 that can be inserted into the outlet tube 8 and a baffle 44 arranged at the other free end of the bracket tube 41; the bracket tube 41 is provided with two air holes 43 to keep the suction tube 2 and the outlet tube 8 in communication, wherein, the suction bin base 6 and the suction bin cover 3 are fixed in a rotary fastening mode, and a first sealing ring 5 is arranged at the connecting part of the suction bin base 6 and the suction bin cover 3, and the first sealing ring plays a role in sealing the connecting part, so that the rotary fastening mode is convenient to assemble or clean: the outer end of the outlet tube 8 is connected to the micro-vacuum pump of the host, and the inner end of the outlet tube 8 is flush with the enclosure plate 62 of the suction bin base 6, and a conical surface 10 is formed on the inner end; the micro-vacuum pump compresses and stretches the air in the pump cavity with a fixed volume to form a vacuum, forming a pressure difference, sucking nasal fluid from the suction tube into the cavity, and discharging gas from the outlet tube; the conical surface 10 facilitates the assembly of the outlet tube and the bracket: the outlet tube 8 and the suction bin base 6 are integrally formed of a PC material, the bracket 4 is made of a PC material, and the outlet tube 8 is provided with a second sealing ring 7 below the conical surface 10, which further improves the sealing performance; the bracket also includes an integrally formed baffle.I42, the baffleI42 is smaller than the baffle 44, and the air hole 43 is between the baffle 44 and the baffle I42, the baffle I also plays a certain blocking role, isolating the possible contact between the stored nasal fluid and the air holes in the process of shaking the nasal aspirator, and the air holes are arranged between the baffle and the baffle I, effectively preventing the blockage of air holes; the upper surface of the baffle 44 is a curved surface with a high middle position and a low edge position, and the curved surface design plays a drainage role when the nasal aspirator is erected for use; the suction tube 2 and the suction bin cover 3 are integrally formed of a PC material, and the distance from the lower surface of the suction tube 2 to the bottom plate 61 of the suction bin base 6 is the same as the height of the bracket 4.; the lower part of the suction tube 2 is provided with a notch 21, which can prevent the bracket from shifting during use and affect the use effect: the notch ensures the smooth airflow inside the suction tube and the cavity; the suction cavity cover 3 is made of a transparent or semitransparent material, so that the user can observe the nasal fluid storage in the cavity from the outside and clean it in time; the upper part of the suction tube 2 is sleeved with a suction nozzle 1, which is made of silica gel material; the suction nozzle 1 is arranged in a shape of small top and big bottom, which is beautiful in the whole; through the function of the suction nozzle, the mucous membrane inside the nasal cavity can be better protected, and the suction nozzle is arranged in a shape of small top and big bottom, so as to be convenient for reaching into the nasal cavity for operation.

The cavity is used to store the inhaled nasal fluid. Because of the umbrella-shaped bracket, the nasal fluid cannot touch the position of the air hole during normal use and small-angle inclined use, so the nasal fluid cannot enter the host and cause pollution. The nasal aspirator has the advantages of convenient disassembly and assembly, easy cleaning, strong sealing performance and high connection strength, and the suction nozzle can well protect nasal mucosa with good comfort.

When in use, in order to facilitate the understanding of the present application, it is described with reference to the drawings.

The overall design of the bracket is umbrella-shaped, and the air holes are located between the baffle and baffle I. When the nasal aspirator is erected or oscillated at a small angle, the nasal fluid from the upper part and the nasal fluid stored at the lower part cannot directly contact with the air hole, and the nasal fluid cannot enter the host through the air hole and the outlet tube, thus ensuring the cleanliness and hygiene of the host.

The above is only the preferred embodiment of the present application, and it is not intended to limit the present application. For those skilled in the art, the present application can be modified and varied. Any modification, equivalent substitution, improvement, etc. made within the spirit and principle of the present application shall be included in the scope of protection of the present application.

What is claimed is:

1. A nasal aspirator suction bin assembly, comprising:
 a suction bin base, wherein the suction bin base is provided with a first connecting end connected with a suction source host and a second connecting end connected with a suction bin cover, and the suction bin base is connected with the suction bin cover to form a cavity therein, and a middle part of the suction bin base is provided with an outlet tube, which runs through the suction bin base and extends into the cavity, wherein the outlet tube is provided with a second sealing ring, and an upper end of the suction bin cover is provided with a suction tube which runs through the suction bin cover and extends into the cavity, wherein a bracket is arranged in the cavity, and the bracket comprises a bracket tube having a first end, and a second end opposite to the first end, wherein the bracket tube from the first end surrounds an outer surface of the outlet tube, and a first baffle connected to the second end of the bracket tube; at least one air hole is arranged on the bracket tube to keep the suction tube and the outlet tube in communication all the time; the bracket further comprises a second baffle I integrally formed; a cross section of the second baffle I is smaller than that of the first baffle; and the air hole is arranged between the first baffle and the second baffle I.

2. The nasal aspirator suction bin assembly according to claim 1, wherein the suction bin base and the suction bin cover are fixed by rotating and fastening, and a first sealing ring is arranged at the connecting part thereof.

3. The nasal aspirator suction bin assembly, according to claim 1, wherein the outlet tube comprises an outer end and an inner end, opposite to the outer end, wherein the outer end of the outlet tube protrudes outward from the suction bin base to be connected with a micro-vacuum pump of the suction source host, and wherein the inner end of the outlet tube protrudes inward from the suction bin base to extent into the cavity, and wherein the inner end of the outlet tube comprises a conical surface to facilitate an assembly of the outlet tube and the bracket.

4. The nasal aspirator suction bin assembly according to claim 3, wherein the outlet tube and the suction bin base are integrally formed of a Polycarbonate (PC) material, and the bracket is made of a PC material.

5. The suction bin assembly of a nose aspirator according to claim 1, wherein an upper surface of the first baffle is a curved surface with a middle position and a low edge position.

6. The nasal aspirator suction bin assembly according to claim 1, wherein the suction tube and the suction bin cover are integrally formed by a Polycarbonates (PC) material, and a distance from a lower surface of the suction tube to a bottom plate of the suction bin base is the same as a height of the bracket; a lower part of the suction tube is provided with a notch.

7. The nasal aspirator suction bin assembly according to claim 1, wherein the suction bin cover is made of a transparent or semitransparent material.

8. The nasal aspirator suction bin assembly according to claim 1, wherein an upper part of the suction tube is sleeved with a suction nozzle, the suction nozzle is made of a silica gel material, and the suction nozzle is arranged in a shape with a small top and a large bottom.

* * * * *